United States Patent
Harper et al.

(10) Patent No.: US 6,436,091 B1
(45) Date of Patent: Aug. 20, 2002

(54) METHODS AND IMPLANTABLE DEVICES AND SYSTEMS FOR LONG TERM DELIVERY OF A PHARMACEUTICAL AGENT

(75) Inventors: Derek J. Harper, Santa Inez; Charles F. Milo, Atherton, both of CA (US)

(73) Assignee: MicroSolutions, Inc., Goleta, CA (US)

( * ) Notice: Subject to any disclaimer, the term of this patent is extended or adjusted under 35 U.S.C. 154(b) by 0 days.

(21) Appl. No.: 09/442,128

(22) Filed: Nov. 16, 1999

(51) Int. Cl.[7] .................................................. A61K 9/22

(52) U.S. Cl. .................................. 604/892.1; 604/891.1

(58) Field of Search ........................... 604/890.1, 891.1, 604/892.1, 93.01, 118, 181–182, 244, 288.01–288.04; 424/422–424

(56) References Cited

U.S. PATENT DOCUMENTS

| | | | | |
|---|---|---|---|---|
| 3,732,865 A | * | 5/1973 | Higuchi et al. ............. | 424/433 |
| 4,034,756 A | * | 7/1977 | Higuchi et al. ............. | 128/832 |
| 4,210,139 A | * | 7/1980 | Higuchi ...................... | 424/436 |
| 4,587,117 A |   | 5/1986 | Edgren |   |
| 4,857,059 A | * | 8/1989 | Rey et al. .................... | 604/185 |
| 4,865,845 A | * | 9/1989 | Eckenhoff et al. |   |
| 5,728,396 A |   | 3/1998 | Peery et al. |   |
| 5,800,422 A | * | 9/1998 | Dong et al. ............... | 604/892.1 |
| 5,801,188 A |   | 9/1998 | Hassenbusch, III et al. |   |
| 5,869,097 A |   | 2/1999 | Wong |   |
| 6,287,295 B1 | * | 9/2001 | Chen et al. ............... | 604/892.1 |

OTHER PUBLICATIONS

Meert TF; De Kock M, Potentiation of the Analgesic Properties if Fentanyl–like Opioids With Alpha 2–adrenoceptor Agonists in Rats, Anesthesiology 19994 Sep; 81(3):677–88.

F. Theeuwes and S.I. Yum, Principles of the Design and Operation of Generic Osmotic Pumps for the Delivery of Semisolid or Liquid Drug Formulations, Annals of Biomedical Engineering 4, 343–353 (1976).

F.P. Boerma, M.D.; H. Noorduin, M.SC; G. Vanden Bussche, M.D., Epidural Sufentanil for Cancer Pain Control in Outpatients, Regional Anesthesia, Nov.–Dec. 1989, vol. 14, No. 6, pp. 293–297.

Jon P. Monk, rodemary Beresford and Alan Ward, Sufentanil A review of its Pharmacological and Therapeutic Use, Drugs 36:286–313 (1988) 0012–6667/88/0009–0286/$14.00/0 ADIS Press.

(List continued on next page.)

Primary Examiner—Brian L. Casler
Assistant Examiner—Catherine Serke
(74) Attorney, Agent, or Firm—Young Law Firm, P.C.

(57) ABSTRACT

Implantable devices and osmotic pump and catheter systems for delivering a pharmaceutical agent to a patient at selectable rates include an impermeable pump housing and a moveable partition disposed within the housing, the partition dividing the housing into an osmotic driving compartment having an open end and a pharmaceutical agent compartment having a delivery orifice. A plurality of semi permeable membranes may be disposed in the open end of the osmotic driving compartment and a number of impermeable barriers may seal selected ones of the plurality of semi permeable membranes from the patient until breached. Breaching one or more of the impermeable barriers increases the surface area of semi permeable membrane exposed to the patient and controllably increases the delivery rate of the pharmaceutical agent through the delivery orifice and catheter. Each of the plurality of semi permeable membranes may have a selected surface area, composition and/or thickness, to allow a fine-grained control over the infusion rate while the pump is implanted in the patient.

32 Claims, 7 Drawing Sheets

OTHER PUBLICATIONS

Word Wide Web page: Mercier FJ, Dounas M, Bouaziz H, Des Mesnard–Smaja V, Foiret C, Vestermann MN, Fischler M, Benhamou D, The effect of adding a minidose of clonidine to intrathecal sufentanil for labor analgesia, Anesthesiology 1998 Sep; 89(3):594–601.

Word Wide Web page, Paix A, Coleman A, Lees J, Grigson J. Brooksbank M, Thorne D, Ashby M, Subcutaneous fentanyl and sufentanil infusion substitution for morphine intolerance in cancer pain management, Pain 1995 Nov;63(2):263–9.

* cited by examiner

METHODS AND IMPLANTABLE DEVICES AND SYSTEMS FOR LONG TERM DELIVERY OF A PHARMACEUTICAL AGENT

BACKGROUND OF THE INVENTION

1. Field of the Invention

This invention relates to the field of drug delivery. In particular, the present invention relates to methods, devices and systems adapted to sub-chronic implantation (less than or equal to 12 months and typically less or equal to about 6 months) in the patient's body to deliver a drug or other pharmaceutical agent at a sustained rate.

2. Description of the Related Art

Since the beginning of modern medicine, drugs have been administered orally. Patients have taken pills as recommended by their physician. The pills must pass through the digestive system and then the liver before they reach their intended delivery site (e.g., the vascular system). The actions of the digestive tract and the liver often reduce the efficacy of medication; furthermore, medications delivered systemically sometimes cause undesirable side effects. Over the course of the past few decades, drug delivery technology and administration has evolved from oral delivery to site-specific delivery. In addition to the oral route of administration, drugs are also routinely administered via the vascular system (intravenous or IV). Intravenous drug delivery has the advantage of bypassing the acidic and enzymatic action of the digestive system. Unfortunately, IV administration requires the use of a percutaneous catheter or needle to deliver the drug to the vein. The percutaneous site requires extra cleanliness and maintenance to minimize the risk of infection. Infection is such a significant risk that IV administration is often limited to a number of weeks, at most. In addition, the patient must wear an external pump connected to the percutaneous catheter.

The next step in the evolution of drug delivery was the implanted pump. The implanted pump is a device that is completely implanted under the skin of a patient, thereby negating the need for a percutaneous catheter. These implanted pumps provide the patient with a drug at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump. Fully implanted constant rate and programmable rate infusion pumps have been sold in the United States for human use since the late 1970s and early 1980s, respectively. Two problems associated with such 1970s and 1980s vintage constant rate and programmable rate infusion pumps relate to their size and their cost. Current implantable constant rate and programmable pumps are about the size and shape of hockey pucks, and they typically are sold to the hospital for $5,000–$9,000. The current implantable pumps must be implanted in the Operating Room under general anesthesia, which further increases costs, as well as the risk, and discomfort to the patient. The size and cost of such pumps has proven to be a substantial barrier to their use, and they are rarely used to deliver medication. An added drawback of phase-change and peristaltic pumps is that they must be refilled with drug every 3–8 weeks. Refills constitute an added burden to the caregiver, and add further costs to an already overburdened healthcare system. The burden associated with such refills, therefore, further limits the use of phase-change and peristaltic pumps.

In the 1970s, a new approach toward implanted pump design was commercialized for animal use only. The driving force of the pumps based upon this new approach utilized the principle of osmosis. Osmotic pumps may be much smaller than other constant rate or programmable pumps, because their infusion rate can be very low. An example of such a pump is described listed in U.S. Pat. No. 5,728,396. This patent discloses an implantable osmotic pump that achieves a sustained delivery of leuprolide. The pump includes an impermeable reservoir that is divided into a water-swellable agent chamber and a drug chamber. Fluid from the body is imbibed through a semi permeable plug into the water-swellable agent chamber and the drug is released through a diffusion outlet at a substantially constant rate.

A limitation of the osmotic pump disclosed in the above-identified patent, however, is that its infusion rate cannot be adjusted once it is implanted. This is acceptable for medications that do not need rate adjustment, but often physicians desire to adjust the infusion rate based on the clinical status of the patient. One example of when a physician would want to increase the infusion rate is in the field of pain management. Implanted pumps can be used to deliver medication to treat pain lasting over an extended period of time. Pain, however, often increases with time, and sometimes patients become tolerant to pain medications; therefore, more medication is needed to effectively treat the pain. The system disclosed in the above-identified patent does not allow a rate increase after implantation, so the physician must either replace the current implant or implant an additional pump to replace or supplement the system. However, the prospect of yet another surgical procedure may cause many patients to forego the potential benefits of the larger dose and may also cause their physicians to advise against the initial procedure altogether. For such patients for whom the implantable pump no longer delivers an adequate dosage of medication, the physician may opt to supplement the dosage delivered by the implantable device by other means, such as by intravenous delivery, in which case the same side effects discussed above may again occur.

Pain management medications are only one example of medications that need to be increased in dosage over time. Other applications may include but are not limited to hypertensive medications, other cardiovascular medications, and medications to treat disorders of the brain and endocrine system.

SUMMARY OF THE INVENTION

An object of the present invention, therefore, is to provide methods and implantable devices and systems for long-term delivery of a pharmaceutical agent at selectable rates. It is another object of the present invention to provide implantable devices and systems for long term delivery of a drug that are small in size and that may be readily implanted in a physician's procedure room or a radiology suite.

In accordance with the above-described objects and those that will be mentioned and will become apparent below, an implantable osmotic pump for delivering a pharmaceutical agent to a patient comprises a pump housing; a moveable partition disposed within the housing, the partition dividing the housing into an osmotic driving compartment having an open end and a pharmaceutical agent compartment having a delivery orifice; a first semi permeable membrane disposed in the open end of the osmotic driving compartment, the first semi permeable membrane being exposed to the patient; a second semi permeable membrane disposed in the open end of the osmotic driving compartment, and a first impermeable barrier disposed over the second semi permeable membrane, the second semi permeable membrane being sealed from the patient until the first barrier is breached, wherein breaching the first barrier increases the surface area of semi permeable membrane exposed to the patient and increases a delivery rate of the pharmaceutical agent through the delivery orifice.

According to further embodiments, the first impermeable barrier may include titanium and/or stainless steel. A saturated solution including NaCl may be present between the first impermeable barrier and the second semi permeable membrane. The first and second semi permeable membranes may the same composition and/or may have the same thickness. Alternatively, the first and second semi permeable membranes may have mutually different compositions and/or mutually different thickness. The pump may further include a third semi permeable member, and a second impermeable barrier may be nested within the first impermeable barrier. The second impermeable barrier may be disposed over the third semi permeable membrane and may seal the third semi permeable membrane from the patient until the second impermeable barrier is breached. Breaching the second barrier increases the surface area of semi permeable membrane exposed to the patient and increases the delivery rate of the pharmaceutical agent through the delivery orifice.

A saturated solution including NaCl may be present between the second barrier and the third semi permeable membrane. The pharmaceutical agent compartment may contain sufentanil, for example, and may also contain other medications. The sufentanil may be at a concentration selected between about 200 µg/mL and about 15,000 µg/mL. The daily delivery rate of the pharmaceutical agent through the delivery orifice may be selected from about 0.5 micrograms per day to about 25 micrograms per day when the pump is configured to be implanted intraventricularly; about 0.5 micrograms per day to about 50 micrograms per day when the pump is configured to be implanted intrathecally; about 5 micrograms per day to about 300 micrograms per day when the pump is configured to be implanted epidurally; about 10 micrograms per day to about 300 micrograms per day when the pump is configured to be implanted subcutaneously.

The first and second semi permeable membranes may include cellulose acetate. The first semi permeable membrane may be shaped as a torus and may be disposed adjacent the outer periphery of the first impermeable barrier. The second semi permeable membrane may be disposed in the center opening of the torus.

A catheter may be coupled to the delivery orifice and the catheter may have an inner diameter of between about 0.001 inches and about 0.010 inches. The catheter may include a guidewire lumen and a pharmaceutical agent infusion lumen. The pharmaceutical agent infusion lumen may have an inner diameter selected between about 0.001 inches to about 0.010 inches. The catheter and the pump may be dimensioned to infuse a volume of pharmaceutical agent of between about 1 µL/day and about 10 µL/day over a treatment period. The catheter and the pump may be dimensioned to infuse a dose of pharmaceutical agent of between about 0.5 µg/day and about 300 µg/day over a treatment period.

At least a portion of the catheter may be radiopaque. The guidewire lumen may include a valve to prevent back flow of fluid into the guidewire lumen.

The present invention is also a method for achieving an analgesic effect in a patient. The method comprises the step of administering a therapeutically effective dose of a sufentanil-containing analgesic to the patient using a device that is fully implanted in the patient. The dose may be administered intravascularly, subcutaneously, epidurally, intrathecally or intraventricularly. A step of selectively increasing the dose in a stepwise manner over a treatment period without removing the device from the patient may also be carried out. The dose may be administered using an implanted osmotic pump that includes a first semi permeable membrane exposed to the patient and a second semi permeable membrane initially not exposed to the patient and wherein the increasing step may include a step of exposing the second semi permeable membrane to the patient. The second semi permeable membrane exposing step may include a step of breaching an impermeable barrier sealing the second semi permeable membrane from the patient. The breaching step may include a step of puncturing the impermeable barrier using a lancet while the pump remains implanted in the patient. The therapeutically effective dose may be selected within the range of about 0.5 µg/day to about 300 µg/day.

According to another embodiment, the present invention may also be viewed as a method for achieving an analgesic effect in a patient, the method comprising intraspinal administration of a therapeutically-effective dose of an analgesic to the patient by an osmotic pump and catheter integrated combination, the pump including a first semi permeable membrane across which an osmotic pressure gradient develops when the pump is implanted in the patient.

The method may also include the step of selectively increasing a surface area of semi permeable membrane exposed to the patient in a stepwise manner. The analgesic may include sufentanil and/or other medication(s). A second semi permeable membrane may be provided, and the surface area of semi permeable membrane exposed to the patient may be increased by breaching an impermeable barrier initially sealing the second semi permeable membrane from the patient. For example, the impermeable barrier may be breached by puncturing the impermeable barrier. The dose may be increased in a stepwise manner by sequentially breaching one of a plurality of nested impermeable barriers disposed over a corresponding plurality of the semi permeable membranes, each sequential breach exposing additional surface area of semi permeable membrane to the patient. Each of the plurality of nested barriers may be configured to be breached by a lancet, an outer diameter of the lancet determining which of the plurality of nested barriers is breached. The analgesic may be administered intravascularly, subcutaneously, epidurally or intrathecally. The second semi permeable membrane may have the same or a different composition as the first semi permeable membrane. Similarly, the second semi permeable membrane may have the same or a different thickness as the first semi permeable membrane.

The present invention is also an integrated implantable pump and catheter system for delivering a dose of sufentanil to a patient over a treatment period, comprising a pump housing; a moveable partition disposed within the housing, the partition dividing the housing into an driving engine compartment and a pharmaceutical agent compartment having a delivery orifice; a catheter coupled to the delivery orifice, and a preloaded amount of sufentanil in the pharmaceutical agent compartment.

The pump and the catheter may be dimensioned to deliver sufentanil at an infusion rate of about 0.5 µg/day to about 300 µg/day over a treatment period. The system further may further include a mechanical infusion rate selection structure configured to allow the infusion rate of the pump to be increased while the system is implanted in the patient. The infusion rate selection feature may include a plurality of semi permeable membranes across each of which osmotic pressure develops when selectively and sequentially exposed to the patient. Each of the plurality of semi permeable membranes may have the same or a different thickness, composition and surface area, the selected thickness, composition and surface area contributing to a rate at which the sufentanil is infused into the patient.

The present invention also encompasses a kit comprising an osmotic pump; sufentanil preloaded in the osmotic pump, and a delivery catheter configured to be coupled to the osmotic pump. The osmotic pump may include a mechanical infusion rate selection structure. The kit may further include a lancet configured to act upon the infusion rate selection structure to increase an infusion rate of the sufentanil through the delivery catheter. The pump may be configured to deliver sufentanil at an infusion rate of about 0.5 μg/day to about 300 μg/day over a treatment period. The catheter may include a guidewire lumen and a sufentanil delivery lumen. The kit may further include a guidewire. The kit may also include a guidewire, a needle and a splittable introducer. According to still further embodiments, the needle may be a hypodermic needle or a non-coring needle, for example.

The present invention is also a kit comprising an osmotic pump that includes a mechanical infusion rate selection structure; an amount of pharmaceutical agent preloaded into the pump, and a delivery catheter. The pharmaceutical agent may include sufentanil and/or other medication(s). The infusion rate selection structure may be configured to allow the infusion rate to be increased while the pump is implanted into a patient. The infusion rate selection structure may include a plurality of semi permeable membranes, each of which being selectably exposable to the patient to increase a dose of pharmaceutical agent delivered to the patient. Each of the plurality of semi permeable membranes may have an individually selected thickness, composition and/or surface area.

According to a still further embodiment thereof, the present invention is a method of delivering a pharmaceutical agent to a patient, comprising the steps of implanting an osmotic pump within the patient, the osmotic pump including the pharmaceutical agent and a plurality of semi permeable membranes across which osmotic pressure develops when exposed to the patient, and controlling a surface area of semi permeable membrane exposed to the patient to control an infusion rate of the pharmaceutical agent analgesic to the patient. A step of controlling the thickness and/or a composition of each of the plurality of semi permeable membranes may also be carried out.

BRIEF DESCRIPTION OF THE DRAWINGS

For a further understanding of the objects and advantages of the present invention, reference should be made to the following detailed description, taken in conjunction with the accompanying figures, in which.

DESCRIPTION OF THE INVENTION

Figure 1:
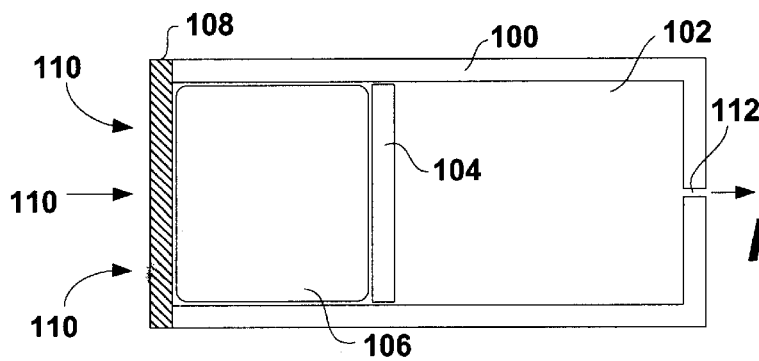
FIG. 1 is a schematic diagram illustrating a conventional drug delivery osmotic pump.

FIG. 1 shows a schematic diagram of a conventional osmotic pump. The pump includes a housing 100. The housing 100 may be shaped as a cylinder and may be divided into a drug reservoir 102 and an osmotic engine compartment 106. A piston 104 separates the drug reservoir 102 and the osmotic engine compartment 106. The movement of the piston 104 toward the delivery orifice 112 provides the driving force to effuse the drug contained within the drug reservoir 102. A semi permeable membrane 108 is disposed at one end of the pump, covering the opening thereof opposite the delivery orifice 112. The semi permeable membrane 108 is permeable to water. Therefore, when the pump is placed within the patient's body or other aqueous medium, water tends to cross the semi permeable membrane 108 into the osmotic engine compartment 106. The osmotic engine within the compartment 106 is the driving force that maintains the solution inside the pump (but outside the reservoir 102) at a fully saturated state. A fully saturated state ensures that the osmotic pressure differential between the body tissue and the inside of the pump remains constant. The pressure differential is maintained constant by a block of osmotic agent (e.g., a salt block) inside of the osmotic agent compartment 106. In operation, the piston 104 slides within the housing toward the delivery orifice 112 as water from the patient's body crosses the semi permeable membrane 108. In turn, the sliding piston 104 causes the drug within the reservoir 102 to effuse from the delivery orifice 112.

Figure 2:
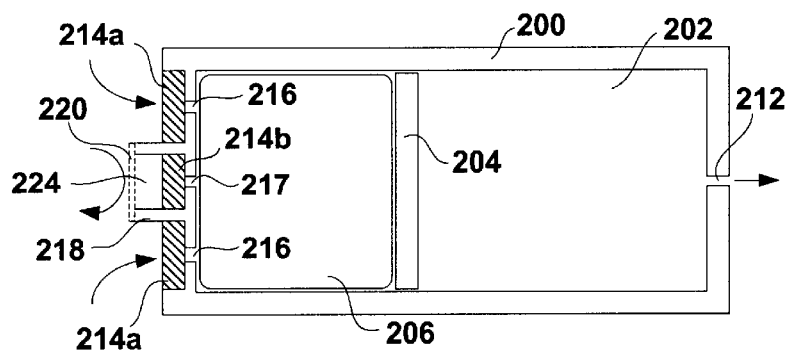
FIG. 2 is a block diagram illustrating an implantable pump for long-term delivery of a pharmaceutical agent at selectable rates according to an embodiment of the present invention, wherein an impermeable barrier is disposed across an underlying central semi permeable membrane.

FIG. 2 is a block diagram illustrating an implantable pump for long-term delivery of a pharmaceutical agent (such as a drug or drugs, for example) at selectable rates, according to an embodiment of the present invention. The present invention achieves such selectable effusion rates by exploiting the property of osmotic pumps that the effusion rate of the drug from the pump of is substantially proportional to the surface area (among other factors, such as composition and thickness) of the semi permeable membrane (such as cellulose acetate, for example) exposed to the patient or other aqueous solution. The implantable pump according to an embodiment of the present invention, as shown in FIG. 2, includes an impermeable rigid (and cylindrical, for example, although other shapes are also possible) pump housing 200 that is internally divided into a pharmaceutical agent compartment 202 and an osmotic driving compartment 206. A piston or other moveable partition 204 separates the pharmaceutical agent compartment 202 from the osmotic driving compartment 206. The pharmaceutical agent compartment 202 includes a delivery orifice 212 through which the pharmaceutical agent is delivered. The delivery orifice 212 may be coupled to a catheter (not shown in FIG. 2) to deliver the pharmaceutical agent from the delivery orifice 212 to a selected location (subcutaneously, epidurally, subdurally, in the subarachnoid space or thecal sac, intravenously or intraventricularly, for example) within the patient. The osmotic driving compartment 206 includes an open end within which a plurality of semi permeable membranes (two such semi permeable membranes 214a, 214b being shown in FIG. 2) is disposed. At least a portion of a peripheral semi permeable membrane 214a is initially exposed to the patient, thereby allowing a net influx of water from the patient's body through the exposed peripheral semi permeable membrane 214a to the osmotic driving engine within the osmotic driving engine compartment 206. As water from the patient's body crosses the exposed peripheral semi permeable membrane 214, the moveable partition 204 is driven toward the delivery orifice 212, constrained in its motion by the pump housing 200. As the pump housing 200 is rigid, a volume of pharmaceutical agent substantially equal to the increase in volume of the osmotic engine is displaced and pushed out of the pump through the delivery orifice 212.

A plurality of semi permeable membranes may be disposed across the open end of the osmotic driving compartment 206. At least one of these semi permeable membranes may be covered by an impermeable barrier, such as shown at 220 in FIG. 2. The barrier 220 may be formed of a biologically inert material that is impermeable to water and/or other bodily fluids that may be found in the patient's body at the location wherein the pump is implanted. For example, the impermeable barrier 220 may include titanium and/or stainless steel. As shown in FIG. 2, the impermeable barrier 220 may be disposed away from the surface of the semi permeable membranes by a spacer 218. The spacer 218 may be shaped as a cylinder supporting the impermeable barrier 220 above the central semi permeable membrane 214b underlying the barrier 220. The impermeable barrier 220 may be sealed to the spacer 218 such as to seal the central semi permeable membrane 214b from the patient. Indeed, as long as the impermeable barrier 220 is intact, there is no (or substantially no) net influx of water from the patient into the osmotic engine through the central semi permeable membrane 214b. When the impermeable barrier 220 is intact, however, water reaches the osmotic engine only through a plurality of openings 216 aligned with the peripheral semi permeable membrane 214a, the openings 216 being defined in the structure supporting the spacer 218 across the open end of the osmotic driving compartment 206. The interstitial space 224 between the impermeable barrier 220 and the surface of the central semi permeable membrane 214b may include a saturated saline solution, to prevent the underlying semi permeable membrane 214b from drying out and to maintain solutions of equal osmolarity on either side of the central semi permeable membrane 214b. The peripheral semi permeable membrane 214a may be a torus-shaped (doughnut-shaped) membrane disposed adjacent an outer periphery of spacer 218 sealing the underlying central semi permeable membrane 214b from the patient. The spacer 218 (and thus the central semi permeable membrane 214b) may be disposed in the center opening of the torus-shaped peripheral permeable membrane 214a. The underlying central semi permeable membrane 214b, therefore, may be concentric with the peripheral permeable membrane 214a.

Figure 3:
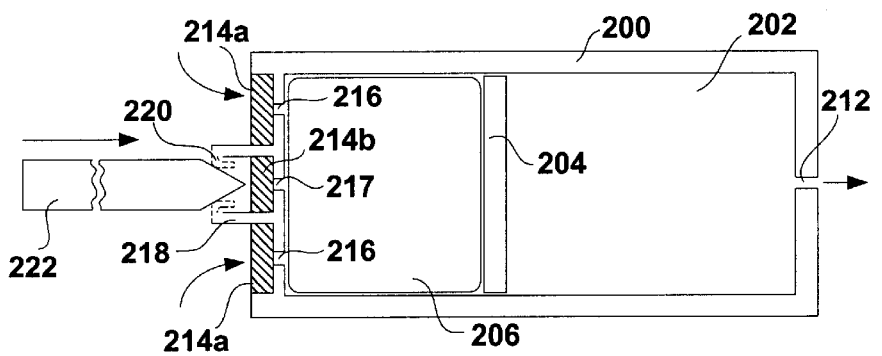
FIG. 3 is a block diagram illustrating the implantable device of FIG. 2, illustrating the breaching of the impermeable barrier.

There are occasions when the physician may wish to increase the dose of the pharmaceutical agent initially delivered to the patient, such as when the level of pain experienced by the patient increases, as a result of the progression of the patient's disease or habituation, for example. Previously, increasing the infusion dose of an osmotic pump entailed subjecting the patient to a further procedure to remove the previously implanted pump to substitute therefor a new pump that delivers a larger dose. According to an embodiment of the present invention, however, the physician may increase the dose of pharmaceutical agent delivered while the pump disclosed herein remains implanted within the patient through a simple and short procedure that may be carried out within the physician's office or in a radiology suite, for example. Indeed, when the physician wishes to increase the delivery rate of the pharmaceutical agent through the delivery orifice 212 (or a catheter coupled thereto), the impermeable barrier 220 may be breached percutaneously by a thin, elongated and rigid member 222 (hereafter lancet), as shown in FIG. 3. Preferably, the outer diameter of the lancet 222 is somewhat greater than the inner diameter of the spacer 218. These relative dimensions prevent the lancet 222 from being inserted too far. That is, the relative dimensions of the lancet 222 and the spacer 218 are such that when the lancet 222 is percutaneously inserted in the patient to breach the impermeable barrier 220, the spacer 218 prevents the lancet 222 from damaging the underlying central semi permeable membrane 214b, breaching the osmotic driving compartment 206 or otherwise damaging the pump. Preferably, the lancet 222 is inserted only as far as to breach the impermeable barrier 220 and to allow a free influx of water from the patient's body into the previously sealed interstitial space 224 between the underlying central semi permeable membrane 214b and the impermeable barrier 220.

Figure 4:
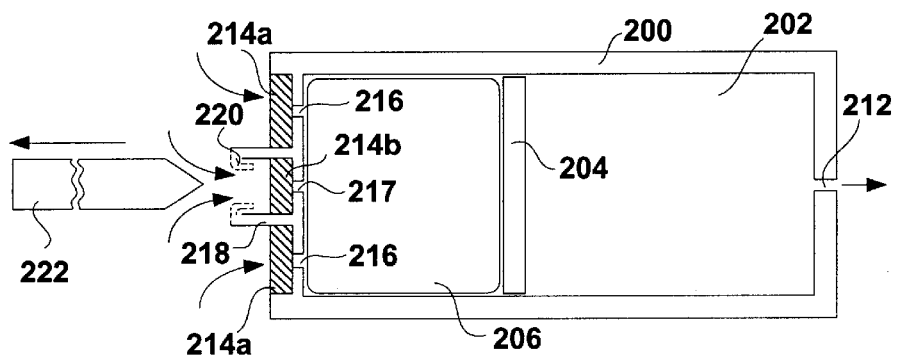
FIG. 4 is a block diagram illustrating the implantable device of FIG. 3, wherein the impermeable barrier is breached, thereby increasing the aggregate surface area of semi permeable membrane exposed to the patient.

When the impermeable barrier 220 is breached and the lancet 222 is retracted from the spacer 218, water from the patient's body reaches the central semi permeable membrane 214b, as indicated by the arrows pointing within the spacer 218 shown in FIG. 4. The effect of breaching the impermeable barrier 220 and allowing water to reach the central semi permeable membrane 214b is to increase the net surface area of semi permeable membrane exposed to the patient. Indeed, once the impermeable barrier 220 is breached, the aggregate surface area of semi permeable membrane exposed to the patient is substantially equal to the sum of the surface areas of the peripheral and central semi permeable membranes 214a and 214b. When the barrier 220 is breached, water from the patient also reaches the osmotic engine through openings 217 aligned with the semi permeable membrane 214b. Increasing the surface area of semi permeable membrane exposed to the patient, therefore, increases the influx of water therethrough, which in turn increases the delivery rate of the pharmaceutical agent through the delivery orifice 212. Thus, the effusion rate of the pump according to the present invention has been increased without removing the pump from the patient, thereby affording the patient an increased dose of pharmaceutical agent (such as an analgesic, for example). The surface area, thickness and/or composition of the semi permeable membranes 214a and 214b may be manipulated to achieve a fine-grained control over the effusion rate of the pharmaceutical agent from the orifice 212 and any catheter coupled thereto.

Figure 5:
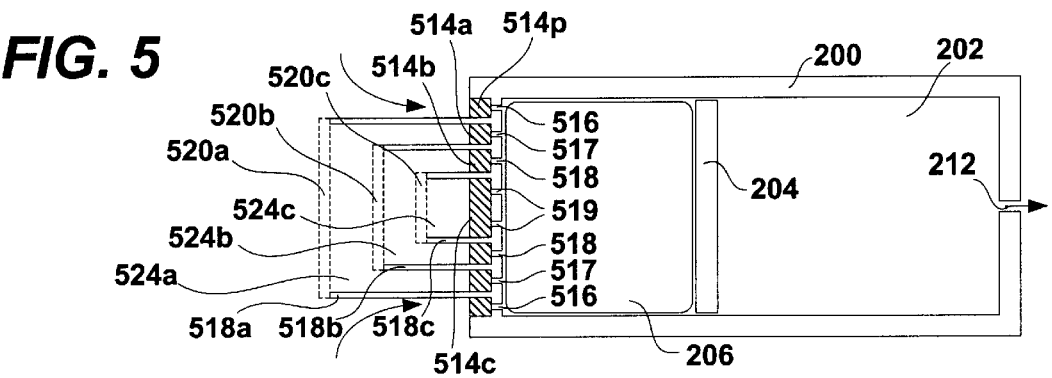
FIG. 5 is a block diagram of an implantable pump for long-term delivery of a pharmaceutical agent at selectable rates according to another embodiment of the present invention, wherein the pump includes a plurality of nested impermeable barriers disposed over and sealing respective underlying semi permeable membranes.

The embodiment of the present invention shown in FIGS. 2 through 4 allows a one step increase in the dose of pharmaceutical agent delivered to the patient, from a first initial dose to a subsequent second, larger dose. However, the present invention is not limited to a one step increase in the dose of pharmaceutical agent delivered to the patient. Indeed, FIGS. 5 though 8 illustrate another embodiment of the present invention wherein the dose delivered to the patient may be increased in situ three times, from a first initial dose to a fourth dose, each subsequent dose being larger than the previous dose. The present invention may also readily be configured for a lesser or greater number of physician-selectable effusion rates. Turning first to FIG. 5, reference numerals 200, 202, 204, 206 and 212 denote structures finding exact counterparts in FIGS. 2 through 4. The description above of the structures referenced by these numerals is, therefore, incorporated herein by reference.

Rather than the single spacer 218 supporting a single impermeable barrier 220 as illustrated in FIGS. 2–4, the embodiment of FIGS. 5 through 8 includes three such spacers, each of which supports a separate and distinct impermeable barrier. Indeed, the pump of FIGS. 5 through 8 includes a first spacer 518a that supports a first impermeable barrier 520a. Nested within the first spacer 518a, according to the embodiment shown in FIGS. 5 through 8, is a second spacer 518b that supports a second impermeable barrier 520b. In turn, nested within the second spacer 518b is a third spacer 518c that supports a third impermeable barrier 520c. Each of the barriers 520a, 520b and 520c is sealed to its respective spacer 518a, 518b and 518c. Disposed within the open end of the osmotic driving compartment 206 is a plurality of separate semi permeable membranes. As shown in FIG. 5, a peripheral semi permeable membrane 514p is disposed adjacent an outer periphery of the base of the first spacer 518a. At least a portion of the peripheral semi permeable membrane 514p is exposed to the patient environment when the pump is initially implanted into the patient. Therefore, water or other aqueous fluid from the patient that has traveled through the peripheral semi permeable membrane 514p may reach the osmotic driving engine within the compartment 206 through the openings 516 facing the peripheral semi permeable membrane 514p. The openings 516 are defined by the pump housing 200 and the structure supporting the spacer 518a across the open end of the osmotic driving compartment 206. In the state of the pump illustrate in FIG. 5, the patient receives an initial first dose of pharmaceutical agent, the dose being proportional to the surface area (and/or composition and/or thickness) of the peripheral semi permeable membrane 514p exposed to the patient.

Figure 6:
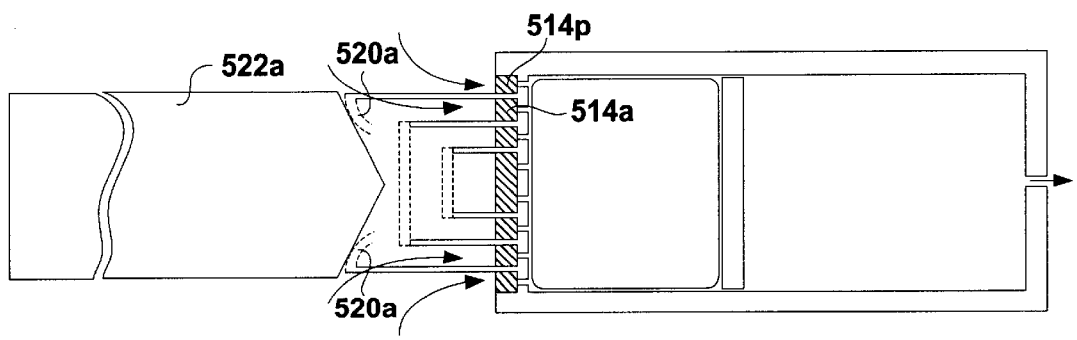
FIG. 6 is a block diagram of the implantable pump of FIG. 5, wherein an outermost impermeable barrier is breached, thereby increasing the aggregate surface area of semi permeable membrane exposed to the patient.

Turning now to FIG. 6, a first lancet 522a may be used to breach the first impermeable barrier 520a. The outer diameter of the lancet 522a is preferably somewhat larger than the inner diameter of the first spacer 518a, so as to cause the lancet 522a to breach only the first impermeable barrier 520a. Once the lancet 522a is retracted from the pump, fluids from the patient may reach the first inner semi permeable membrane 514a. Therefore, water or other aqueous fluid from the patient that has traveled through the first inner semi permeable membrane 514a may reach the osmotic driving engine within the compartment 206 through the openings 517 facing the first inner semi permeable membrane 514a. The aggregate surface area of semi permeable membrane exposed to the patient is, in the state of the pump shown in FIG. 6, the sum of the surface areas of the peripheral semi permeable membrane 514p and the first inner semi permeable membrane 514a. Therefore, the effusion rate of the pharmaceutical agent from the compartment 202 to the patient is now proportional to the increased area (and/or composition and/or thickness) of the semi permeable membrane exposed to the patient, resulting in the delivery of a second dose of pharmaceutical agent, the second dose being greater than the first dose administered when the pump is in the state illustrated in FIG. 5.

Figure 7:
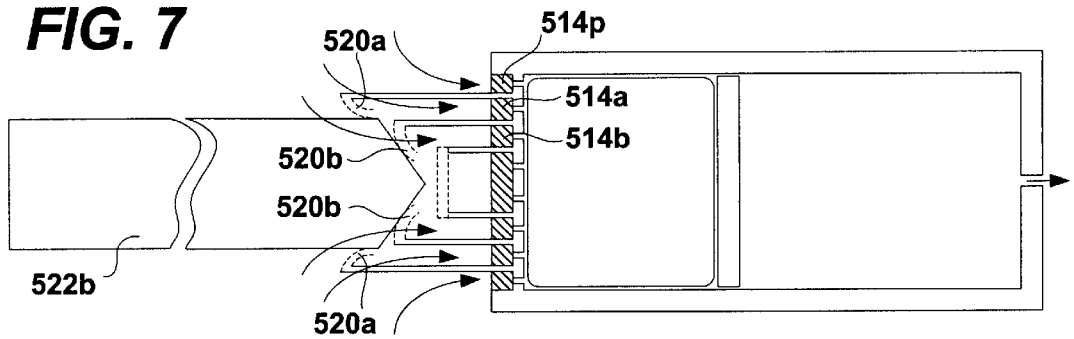
FIG. 7 is a block diagram of the implantable pump of FIG. 6, wherein the middle impermeable barrier is breached; thereby further increasing the aggregate surface area of semi permeable membrane exposed to the patient.

As shown in FIG. 7, a second lancet 522b may be used to breach the second impermeable barrier 520b. The outer diameter of the second lancet 522b is preferably somewhat larger than the inner diameter of the second spacer 518b (and smaller than the inner diameter of the lancet 522a), so as to cause the lancet 522b to breach only the second impermeable barrier 520b. Once the lancet 522b is retracted from the pump, fluids from the patient environment in which the pump is implanted may also reach the second inner semi permeable membrane 514b. Therefore, water or other aqueous fluid from the patient that has traveled through the second inner semi permeable membrane 514b may reach the osmotic driving engine within the compartment 206 through the openings 518 facing the second semi permeable membrane 514b. The surface area of semi permeable membrane exposed to the patient is, in the state of the pump shown in FIG. 7, the sum of the surface areas of the peripheral semi permeable membrane 514p, the first inner semi permeable membrane 514a and the second inner semi permeable membrane 514b. Therefore, the effusion rate of the pharmaceutical agent from the compartment 202 to the patient is now proportional to this increased area (and/or composition and/or thickness) of semi permeable membrane exposed to the patient, thereby resulting in the delivery of a third dose of pharmaceutical agent, the third dose being greater than either of the first and second doses administered when the pump is in the states illustrated in FIGS. 5 and 6.

Figure 8:
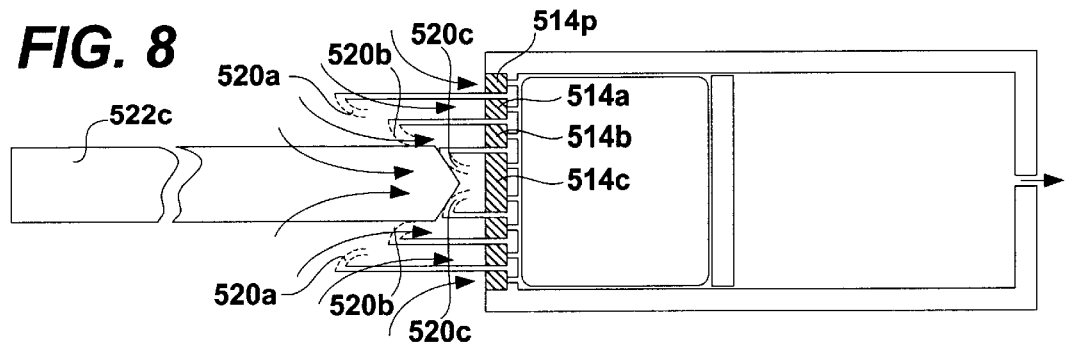
FIG. 8 is a block diagram of the implantable pump of FIG. 7, wherein the innermost impermeable barrier is breached; thereby still further increasing the aggregate surface area of semi permeable membrane exposed to the patient.

Similarly, as shown in FIG. 8, a third lancet 522c may be used to breach the third impermeable barrier 520c. The outer diameter of the lancet 522b is preferably somewhat larger than the inner diameter of the third spacer 518c (and smaller than the inner diameter of the first or second effusion pens 522a, 522b), so as to cause the lancet to breach only the third impermeable barrier 520c without, however, damaging the third semi permeable membrane 514c. Once the lancet 522c is retracted from the pump, fluids from the patient environment in which the pump is implanted may also reach the third inner semi permeable membrane 514c. Therefore, water or other aqueous fluid from the patient that has traveled through the third inner semi permeable membrane 514c may reach the osmotic driving engine within the compartment 206 through the openings 519 facing the third inner semi permeable membrane 514c. The surface area of semi permeable membrane exposed to the patient is, in the state of the pump shown in FIG. 8, the sum of the surface areas of the peripheral semi permeable membrane 514p, the first semi permeable membrane 514a, the second semi permeable membrane 514b and the third semi permeable membrane 514c. Therefore, the effusion rate of the pharmaceutical agent from the compartment 202 to the patient is now proportional to this increased area (and/or composition and/or thickness) of semi permeable membrane exposed to the patient, thereby resulting in the delivery of a fourth dose of pharmaceutical agent, the fourth dose being greater than the first, second or third doses administered when the pump is in the states illustrated in FIGS. 5, 6 and 7. A saturated saline solution is present in each of the interstitial spaces shown at reference numerals 524a, 524b and 524c.

The peripheral semi permeable membrane 514p may be a torus-shaped membrane disposed adjacent the outer periphery of the first spacer 518a. Likewise, the first semi permeable membrane 514a may be a torus-shaped membrane disposed adjacent an outer periphery of the second spacer 518b. Similarly, the second semi permeable membrane 514b may be a torus-shaped membrane disposed adjacent an outer periphery of the third spacer 518c. The third semi permeable membrane 514c may be shaped as a right cylinder or a disk disposed within the open end of the osmotic driving compartment 206, aligned with the third spacer 518c. The semi permeable membranes 514p, 514a, 514b and 514c may, therefore, be concentrically disposed relative to one another. Moreover, each of the semi permeable membranes 514p, 514a, 514b and 514c may have a different surface area and/or thickness and/or composition, thereby allowing a high degree of control over the effusion rate of the pharmaceutical agent to the patient.

Various modifications to the above-described pump may occur to those of skill in this art. For example, the pump housing 200 may be extended at least as far as to cause the proximal edge thereof (the proximal end of the pump being defined as that end of the pump that is closest to the semi permeable membranes and the distal end thereof being defined as that end that is closest to the delivery orifice 212) to be coplanar with the first impermeable barrier 520a, to protect the nested spacers 518a, 518b and 51 8c and to provide additional rigidity to the pump. Also, the lancets 522a, 522b and 522c may be combined in a single adjustable device, wherein structural characteristics of the lancet such as the diameter of the device and/or the length to which it penetrates within the nested spacer structures 518a, 518b and 518c may be selectively adjusted by the physician depending upon the dose of pharmaceutical agent to be delivered. For example, such structural characteristics may be selected on such a lancet by "dialing"the selected dose increase on the lancet on an adjusting wheel or dial integrated in the pen.

Figure 9A:
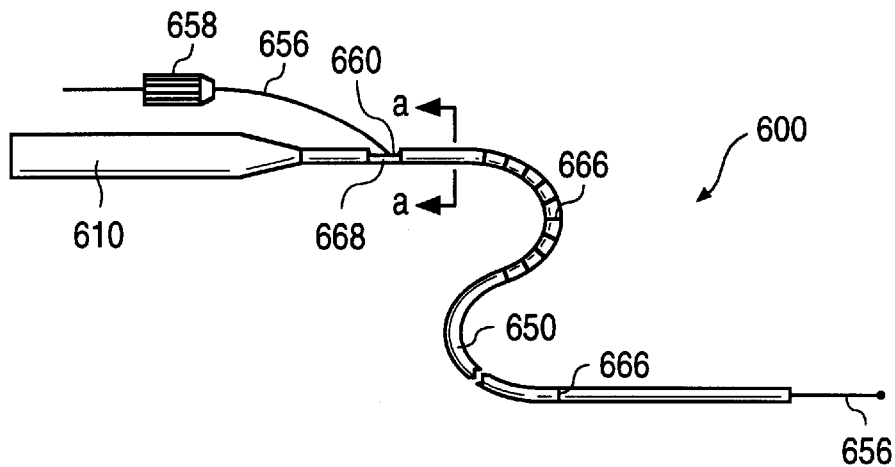
FIG. 9A is a diagram of a complete implantable pump and catheter system for long-term delivery of a pharmaceutical agent at selectable rates, according to an embodiment of the present invention.
Figure 9B:
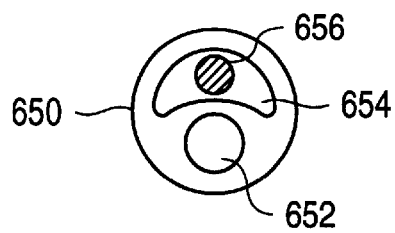
FIG. 9B is a cross-sectional view of the catheter portion of the implantable pump of FIG. 9A, taken along lines AA'.

FIG. 9A is a diagram of a complete fully implantable pump and catheter assembly 600 for long-term delivery of a pharmaceutical agent at selectable rates, according to an embodiment of the present invention. As shown, the implantable pump includes two major portions: the pump 610 and the catheter 650. The pump 610 and the catheter 650, according to an embodiment of the present invention, are preferably coupled together, so that the physician needs not perform any assembly before implanting the device into the patient. Moreover, the pharmaceutical agent may be preloaded into the compartment 202 (see FIGS. 2 through 8) of pump 610 to allow immediate use of the pump and catheter assembly 600 upon unpacking thereof in the physician's procedure room or radiology suite. The pump 610 may include the structures and functionality of the pumps discussed above relative to FIGS. 2–4 and/or FIGS. 5–8. According to an embodiment of the present invention, the catheter 650 may be a dual-lumen catheter. FIG. 9B is a cross-sectional view of such a dual-lumen catheter 650, taken along lines AA' of FIG. 9A. As shown therein, the catheter 650 includes an infusion lumen 652 that is proximately attached to the osmotic pump 610, such as to its delivery orifice 212, as shown in FIGS. 2–8. The pharmaceutical agent, therefore, flows from the pump 610 to the distal end of the catheter 650 (the end thereof farthest away from the pump 610) to be released within the patient (such as within the patient's epidural and/or intrathecal space, for example). The catheter 650 may also include a guidewire lumen 654 through which may be inserted a guidewire 656. The guidewire 656 may be equipped with a guidewire torque 658, to facilitate manipulation of the guidewire 656 within the patient. The guidewire lumen 654 may span at least a portion of the length of the catheter 650. The guidewire 656 may be inserted into the guidewire lumen 654 of the catheter 650 through a guidewire port 660. The guidewire port 660 may be formed, for example, as a slit in the catheter 650.

Figure 9C:
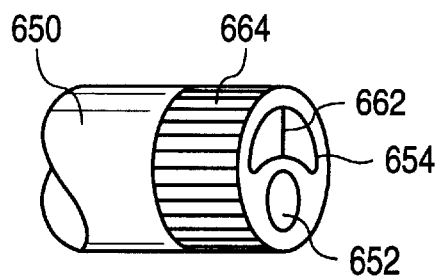
FIG. 9C is a perspective view of the distal end of the catheter portion of the implantable pump of FIG. 9A, according to an embodiment of the present invention.

FIG. 9C is a perspective view of the distal end of the catheter 650 of the implantable pump and catheter assembly of FIG. 9A, according to an embodiment of the present invention. As shown therein, the infusion lumen may terminate as an open lumen, to allow the pharmaceutical agent to exit the catheter 650. The guidewire lumen 654, according to an embodiment of the present invention, may include a distal valve 662, such as a plug of elastomeric material (such as silicone or polyurethane, for example) with a slit therein. The distal valve 662 prevents back flow of the pharmaceutical agent released into the patient through the guidewire lumen 654. Such back flow may occur due to the pressure differential between the patient environment (such as the spinal fluid) and the guidewire port 660. That is, the spinal fluid may be at a higher pressure than the pressure in the guidewire lumen 654 and the outside. In the absence of a distal valve 662 or other means for preventing back flow, the pharmaceutical agent effluent and spinal fluid may tend to flow back proximally toward the pump 610 through guidewire lumen 654 (once implanted). Such a distal valve 662 allows the guidewire 656 to be pushed therethrough but prevents back flow of the pharmaceutical agent or bodily fluids (such as spinal fluid) through the guidewire lumen 654 when the guidewire 656 is removed.

The distal end of the catheter 650, as shown in FIG. 9C, may include a radio opaque marker 664 to allow the distal tip of the catheter 650 to be clearly visible through fluoroscopy.

Such distal marker 664 facilitates the insertion of the catheter portion 650 of the implantable pump 600 and catheter assembly under fluoroscopic guidance in a radiology suite, for example.

To further aid implantation of the pump 600 under fluoroscopic guidance, radio opaque length markers 666 may be disposed on or incorporated within the length of the catheter 650. This allows the physician to gauge the length of catheter 650 inserted into the patient. Alternatively, the entire length of the catheter 650 may include a radio opaque material.

Alternatively still, the distal valve 662 may be omitted, as may be the distal radio opaque marker 664. Instead, the catheter 650 according to the present invention may be radio opaque over at least a portion of its entire length and include a proximal guidewire valve 668 disposed within the guidewire lumen 654 at or adjacent to the guidewire port 660. The combination of a radio opaque catheter 650 and a proximal guidewire valve 668 allows the physician to adjust the length of the catheter 650 by trimming the distal end thereof according to the needs of the procedure at hand and/or the patient's anatomy. Any suitable radio opaque material may be used to render all or a portion or selected portions of the catheter 650 radio opaque. For example, the catheter 650 may be formed of silicone or polyurethane and may be doped with barium sulfate, for example. The length of the catheter 650 may be most any therapeutically effective length. A longer length, however, increases the dead space therein and delays the effusion of the pharmaceutical agent into the patient, as it will take longer for the agent to travel from the delivery orifice 212 to the free distal end of the infusion lumen 652. For example, the catheter 650 may be about 5 cm to about 100 cm in length. More preferably, the catheter 650 may be about 10 cm to about 30 cm in length. More preferably still, the catheter 650 may be about 15 cm to about 25 cm in length. For example, the catheter 650 may be about 20 cm in length. The guidewire 656 may be about 0.014 inches to about 0.038 inches in diameter. The internal diameter (ID) of the infusion lumen 652 may be selected within the range of about 0.001 inches to about 0.010 inches. The walls of the catheter 650 may be about 0.001 inches to about 0.006 inches in thickness. According to an embodiment of the present invention, the outer diameter (OD) of the catheter 650 may be selected between about 0.024 inches and about 0.066 inches in thickness.

Tables 1 and 2 show the time required to infuse the dead space volume of the catheter of the implantable pump system according to the present invention, for an infusion rate of 1.75 and 5 microliters/day (µL/day), respectively.

TABLE 1

1.75 Microliter/Day infusion Rate
Time To Infuse Dead Space Volume of Catheter (in hours)

| Catheter Diameter | Catheter Length (cm) | | | |
|---|---|---|---|---|
| (in.) | 10 | 15 | 20 | 40 |
| 0.001 | 0.7 | 1.0 | 1.4 | 2.8 |
| 0.002 | 2.8 | 4.2 | 5.6 | 11.1 |
| 0.005 | 17.4 | 26.1 | 34.7 | 69.5 |
| 0.010 | 69.5 | 104.2 | 139.0 | 278.0 |

TABLE 2

5 Microliter/Day infusion Rate
Time To Infuse Dead Space Volume of Catheter (in hours)

| Catheter Diameter | Catheter Length (cm) | | | |
|---|---|---|---|---|
| (in.) | 10 | 15 | 20 | 40 |
| 0.001 | 0.2 | 0.4 | 0.5 | 1.0 |
| 0.002 | 1.0 | 1.5 | 2.0 | 3.9 |
| 0.005 | 6.1 | 9.1 | 12.1 | 24.3 |
| 0.010 | 24.3 | 36.5 | 48.7 | 97.3 |

Figure 10:
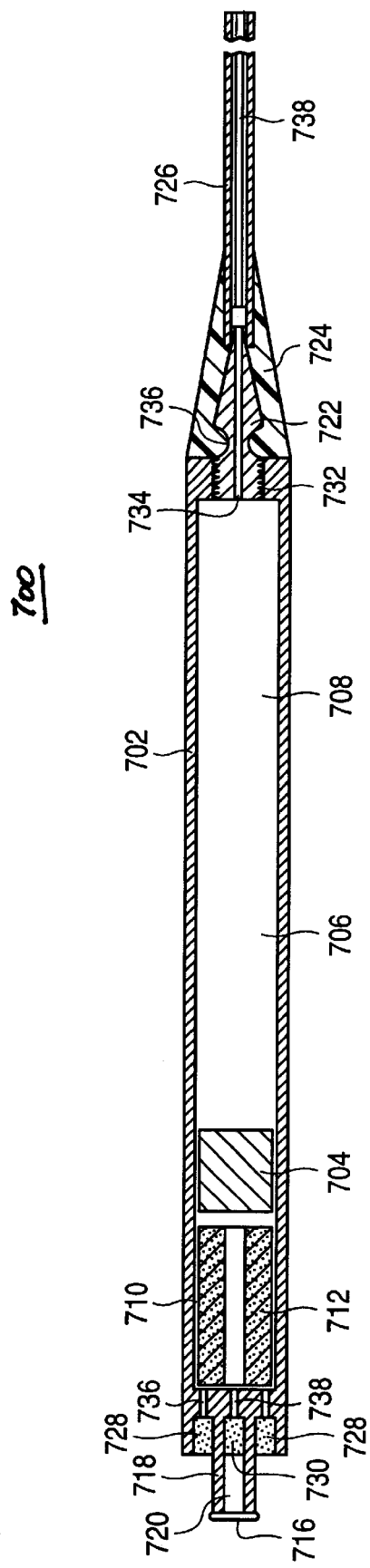
FIG. 10 is a cross-sectional side view of an implantable pump according to an embodiment of the present invention.

FIG. 10 is a cross-sectional view of an implantable pump 700, according to a further embodiment of the present invention. The pump 700 of FIG. 10 includes a rigid pump housing 702. The pump housing 702 encloses a moveable partition 704 that separates a pharmaceutical agent compartment 706 for enclosing a pharmaceutical agent 708 from an osmotic driving compartment 710 for enclosing an osmotic engine 712 (salt block). At the proximal end of the osmotic driving compartment 710 is disposed a pair of semi permeable polymer membranes 728, 730, such as cellulose acetate membranes. The pump 700 may include a peripheral torus-shaped shaped semi permeable membrane (or a plurality of such peripheral semi permeable membranes) 728 and a central semi permeable membrane 730, the latter being surrounded and sealed from the patient by the spacer 718. The peripheral torus-shaped semi permeable membrane 728 is in fluid communication with the osmotic engine through openings 736 and the central semi permeable membrane 730 is in fluid communication with the osmotic engine 712 through openings 738. The spacer 718 supports an impermeable barrier 716 away from the underlying central semi permeable membrane 730. The impermeable barrier 716 may be formed of titanium and/or stainless steel, for example. The interstitial space between the impermeable barrier 716 and the underlying central semi permeable membrane 730 includes a saturated saline solution 720. According to the embodiment of FIG. 10, the distal end of the pump 700 defines a threaded opening 732. A nipple 722 may be screwed onto the threaded opening 732. The nipple 722 may include a centrally-disposed nipple infusion lumen 734. The nipple infusion lumen 734 may be seen as functionally equivalent to the delivery orifice 212 of FIGS. 2 through 8. The nipple 722 may have a shape that tapers distally and may include a proximal recessed feature 736 that allows an elastomeric strain relief element 724 to be snapped and secured thereon. The proximal region of the strain relief element may be flush with the pump housing 702, while the distal end thereof may taper to allow the catheter 726 to be scaled or press-fitted thereto. The distal portion of the catheter 726 is not shown in FIG. 10. The catheter may have a structure similar to that disclosed relative to catheter 650 in FIG. 9. Alternatively, as shown in FIG. 10, the catheter 726 may include a single effusion lumen 738.

Figure 11:
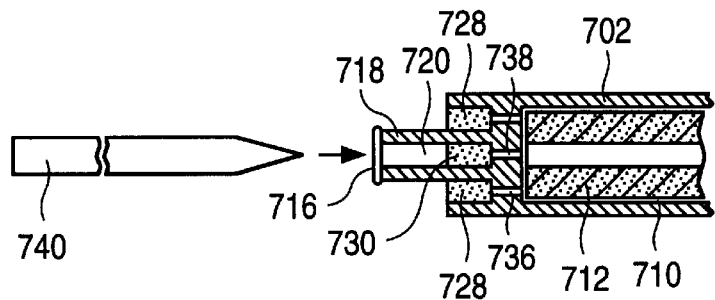
FIG. 11 shows a proximal portion of the implantable pump of FIG. 10, showing the manner in which the pharmaceutical agent (e.g., drug) delivery rate of the pump may be increased, according to an embodiment of the present invention.
Figure 12A:
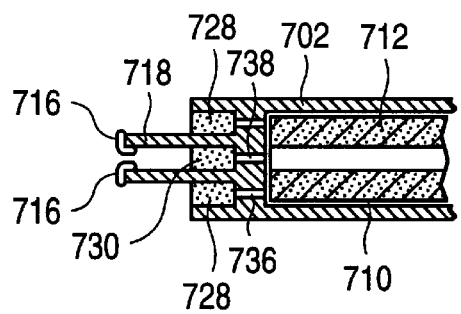
FIG. 12A shows a cross section of the proximal portion of the implantable pump of FIG. 11 after the impermeable barrier has been breached.
Figure 12B:
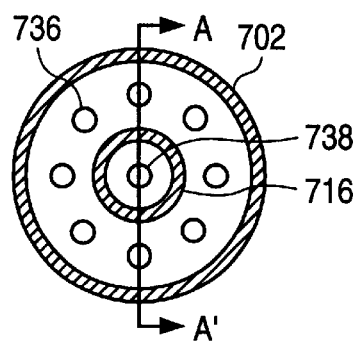
FIG. 12B shows an end view of the implantable pump of FIG. 12A.

FIG. 11 shows a cross section (taken along line AA" of FIG. 12B) of the proximal portion of the implantable pump 700 of FIG. 10, showing the manner in which the pharmaceutical agent delivery (infusion) rate of the pump 700 may be increased, according to an embodiment of the present invention, whereas FIG. 12A shows a cross section (also taken along line AA" of FIG. 12B) of the proximal portion of the implantable pump of FIG. 11 after the impermeable barrier 716 has been breached. When the implantable pump 700 is initially implanted into the patient, only the peripheral semi permeable membrane 728 is exposed to the patient's bodily. The surface area of the torus-shaped (for example) peripheral semi permeable membrane 728 establishes the initial effusion rate of the pharmaceutical agent(s) from the compartment 706. When the lancet 740 breaches the impermeable barrier 716, the surface area of semi permeable membrane exposed to the patient is increased to include the surface area of the central semi permeable membrane 730 as well. According to the present invention, the relative ratio between the surface areas of the semi permeable membranes exposed and not exposed to the patient controls the effusion rate of the pharmaceutical agent from the pump 700. Additionally, by varying the composition and/or thickness (in place of or in addition to the surface areas thereof) of the semi permeable membranes of the present invention, different step effusion rate functions may readily be achieved upon breaching the impermeable barrier(s) of the pump.

Figure 13:
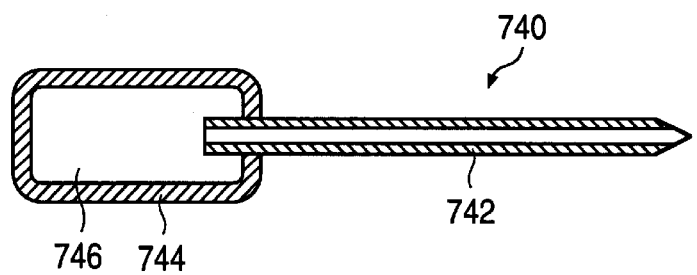
FIG. 13 shows a cross-sectional side view of an embodiment of a lancet that may be utilized to breach the impermeable barrier of the implantable pump, according to an embodiment of the present invention.

FIG. 13 shows an embodiment of a lancet 740 that may be utilized to breach the impermeable barrier 716 of the implantable pump according to the present invention. The lancet 740 may include a hollow cylindrical portion 742 sharpened at its distal end and a reservoir 744. The reservoir 744 may be formed of an elastomeric material (such as silicone, for example), to allow the physician to squeeze the reservoir between his or her fingers. The reservoir 744 may contain water or a saturated saline solution, collectively referenced by the numeral 746 in FIG. 13. When the physician wishes to increase the dose of pharmaceutical agent delivered to the patient, he or she may breach (puncture) the impermeable barrier 716 of the pump 700 using an appropriately dimensioned lancet 740. Thereafter, the reservoir 744 may be squeezed to flush the saline solution contained therein into the interstitial space 720 between the central semipermeable membrane 730 and the impermeable barrier 716. The lancets 222, 522a, 522b and/or 522c or FIGS. 2 through 8 may be configured as shown in FIG. 13a. Alternatively, the aforementioned lancets may include appropriately dimensioned hollow or solid needles, such as hypodermic needles, for example.

Figure 14A:
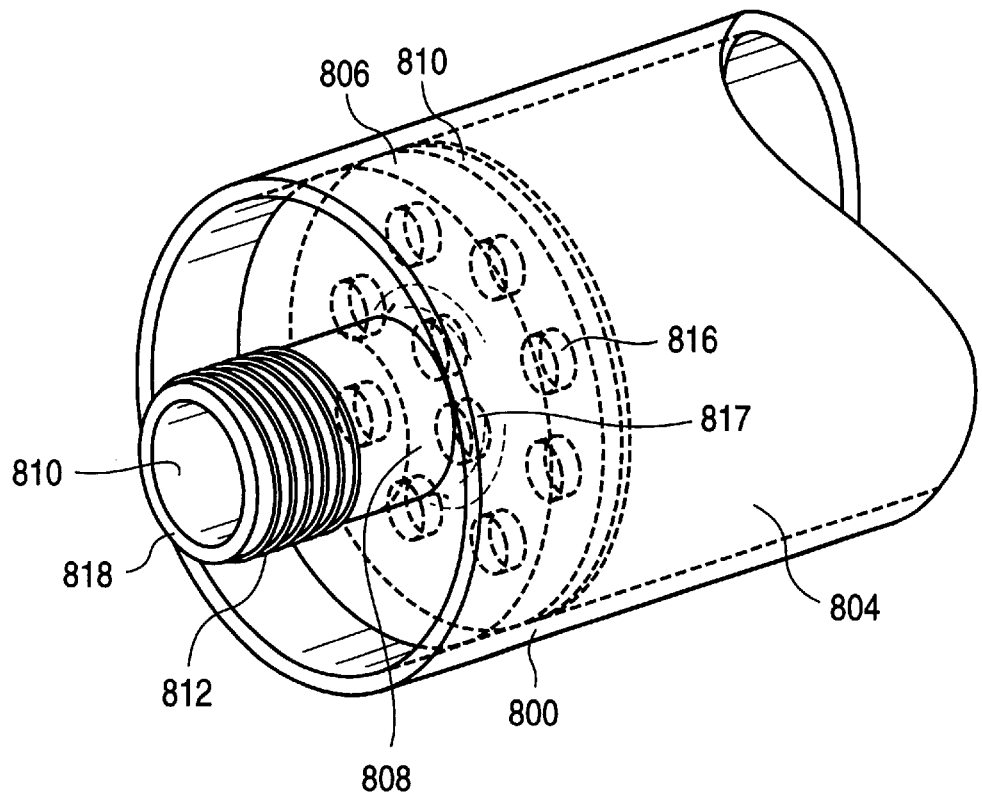
FIG. 14A depicts the proximal portion of an implantable pump for long-term delivery of a drug at selectable rates, wherein the end-cap portion thereof is removed, according to another embodiment of the present invention.
Figure 14B:
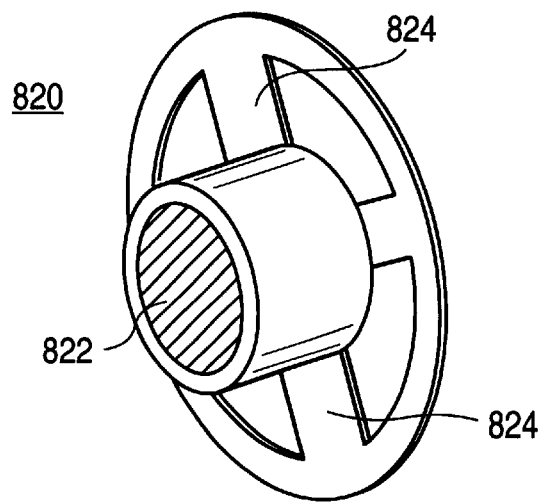
FIG. 14B is a perspective view of the end-cap portion of the implantable pump of FIG. 14A.

FIG. 14A is a perspective view of the proximal portion of an implantable pump for long-term delivery of a pharmaceutical agent at selectable rates, wherein an end-cap portion thereof is removed, to illustrate a further embodiment of the present invention. FIG. 14B is a detail view of an end-cap portion configured to fit on the proximal portion of the pump shown in FIG. 14A. The implantable pump shown in FIG. 14A includes a pump housing 800 that encloses a pharmaceutical agent compartment (not shown in FIG. 14b), a moveable partition or piston (also not shown in FIG. 14a), as well as an osmotic driving compartment enclosing an osmotic engine 804. Semi permeable membranes are disposed adjacent the free end of the osmotic driving engine compartment 802; namely a peripheral semi permeable membrane 806 and a central semi permeable membrane 808. Separating the two semi permeable membranes 806 and 808 is a spacer 810. The spacer 810, as shown in FIG. 14A, may be shaped as a right cylinder, although other spacer shapes are possible. The peripheral semi permeable membrane 806 may be disposed about the base of the spacer 810—that is, in the distal portion thereof. Indeed, the peripheral semi permeable membrane 806 may be disposed adjacent the spacer 810 and around its outer periphery, thereby forming a generally toroidal shape. The central semi permeable membrane 808 may be disposed within the spacer 810, also toward the distal end thereof. The peripheral semi permeable membrane 806 and the central semi permeable membrane 808 may be approximately and mutually co-planar, albeit separated by at least the thickness of the wall of the spacer 810. The generally disc-shaped structure forming the distal base of the spacer 810 defines a plurality of openings 816 aligned with the peripheral semi permeable membrane 806 and a plurality of openings 817 aligned with the central semi permeable membrane 808. The openings 816 allow the influx of water that has traveled from the patient's body through the peripheral semi permeable membrane 806 to reach the osmotic driving compartment 802 and thus to reach the osmotic engine 804. According to an embodiment of the present invention, the impermeable barrier 822 may be fitted onto the free proximal end 818 of the spacer 810. Alternatively, the proximal portion of the spacer 810 may define a threading 812 adapted to receive a mating threaded end-cap 820, as shown in FIG. 14B. As shown in FIG. 14B, the end-cap 820 may fit over and screw on the free proximal end 818 of the spacer 810. The impermeable barrier 822 may be disposed across the end-cap 820. When the end-cap 820 is screwed onto the free proximal end 818 of the spacer 810, the underlying central semi permeable membrane 808 is sealed from the patient's bodily fluids until and if the impermeable barrier 822 is breached. Struts 824 attached to the end-cap 820 may span the distance between the end-cap 820 and the proximal edge of the pump housing 800 to lend additional support and stability to the assembly including the end-cap 820 and the pump housing 800. According to an embodiment of the present invention, the end cap 820 may be welded to the spacer 810 and pump housing 800. As shown, the proximal edge of the pump housing 800 may be approximately coplanar with the proximal free end 818 of the spacer 810. The interstitial space between the end-cap 820 and the underlying central portion 808 of the semi permeable membrane is preferably filled with a saturated solution of relatively high osmolarity, such as sodium chloride (NaCl). When the impermeable barrier 822 is breached, the openings 817 (FIG. 14A) allow the influx of water that has traveled from the patient's body through the central semi permeable membrane 808 to reach the osmotic driving compartment 802 and thus to reach the osmotic engine 804.

Figure 15:
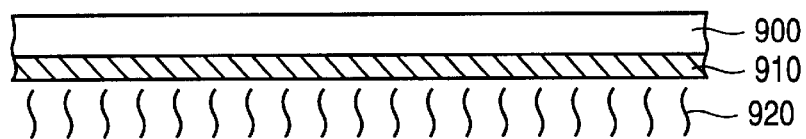
FIG. 15 is a cross-sectional diagram of tissue surrounding the spinal fluid wherein the implantable pump according to the present invention may infuse one or more pharmaceutical agents.

FIGS. 15 through 18 illustrate a method of and kits for implanting an implantable pump for long-term delivery of a pharmaceutical agent at selectable rates, according to the present invention. One method of introducing the pump and catheter combination according to the present invention (shown in FIG. 9a, for example) is known as the "Seldinger Technique" often used to insert catheters through patients' vasculatures. FIGS. 15 through 18 illustrate a method of implanting the pump subcutaneously so the distal free distal end of the integrated catheter lies in the intraspinal space which contains cerebrospinal fluid (hereafter CSF). The integrated catheter may also be inserted epidurally; that is, adjacent the dura matter surrounding the brain and spinal cord. Returning now to FIG. 15, the CSF is contained within the dura matter 910, over which lies a superficial tissue layer 900. FIG. 15 does not show the spinal cord or any of the bony structures thereof.

Figure 16:
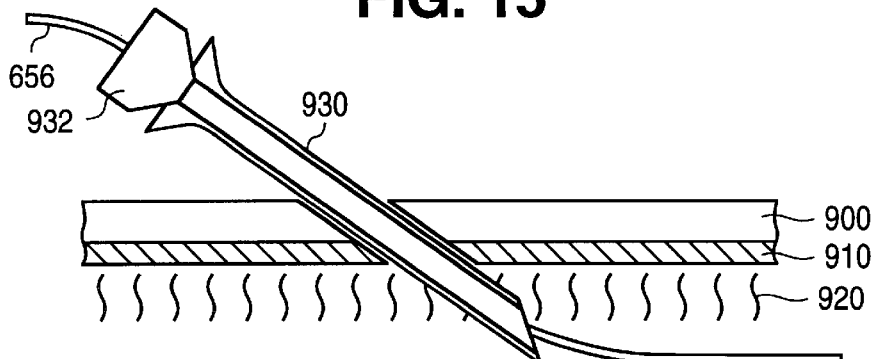
FIG. 16 is a cross-sectional diagram illustrating the first steps in introducing the implantable pump into the tissue of FIG. 15, according to the present invention.
Figure 17:
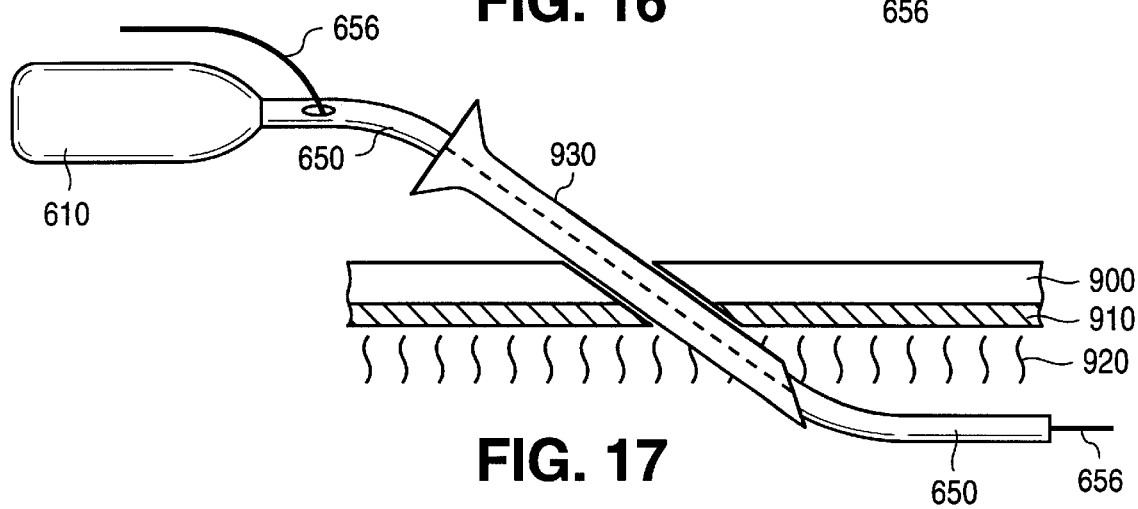
FIG. 17 is a cross-sectional diagram of further steps to be carried out in introducing the implantable pump system of the present invention into the tissue of FIG. 15.
Figure 18:
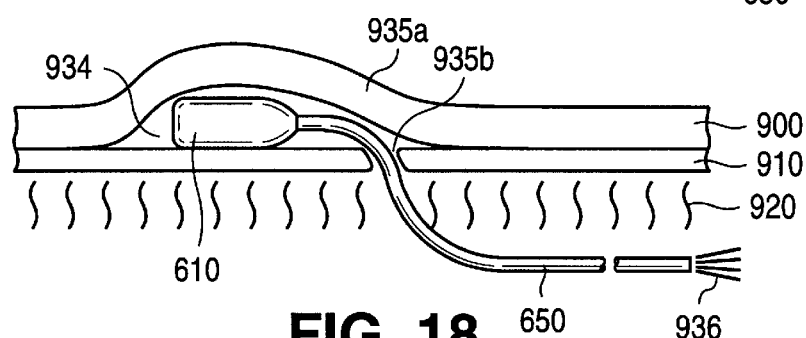
FIG. 18 illustrates a pump for long-term delivery of a pharmaceutical agent at selectable rates according to the present invention, fully implanted into the tissue of FIG. 15.
Figure 19A:
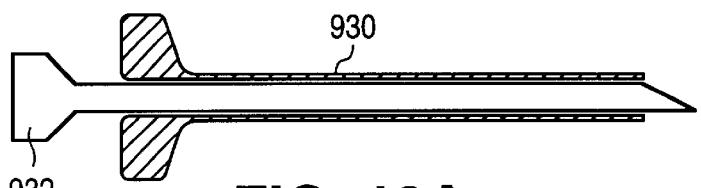
FIG. 19A is a cross-sectional diagram of a split introducer and needle used to insert the catheter into the patient, according to an embodiment of the present invention.
Figure 19B:
FIG. 19B shows a longitudinal cross section of a non-coring needle that may be utilized in combination with the split introducer of FIG. 19A to insert the catheter into the patient, according to another embodiment of the present invention.

As shown in FIG. 16, to insert the integrated pump and catheter assembly according to the present invention, a split introducer 930 and hypodermic needle 932 is inserted through the superficial tissue layer 900 and the dura 910. The preferred split introducer 930 according to the present invention is shown in cross section in FIG. 19. As shown therein, the split introducer 930 has a conical tapered shape to facilitate blunt dissection of the superficial tissue 900 and the dura matter 910, thereby easing the introduction of the catheter (such as shown at 650 in FIG. 9A) therethrough and into the CSF 920. The split introducer 930 may be shaped so as to be in intimate contact with a needle 932 (such as the hypodermic needle shown in FIGS. 16 and 19 or the non-coring needle 932 shown in cross section in FIG. 19, for example), and may become larger towards its proximal end. As the dura matter 910 is very elastic, it tends to recoil as the split introducer 930 is inserted therethrough. The split introducer 930 may blunt dissects the dura matter 910 and may tear it somewhat as it enlarges the passageway through which it tunnels. Alternatively, a non-coring needle (an example of which is shown in cross-section in FIG. 19B) may be used in place of the hypodermic needle shown in FIGS. 16 and 19A. Returning to FIG. 16, a needle 932 is then inserted through the split introducer 930. The needle 932 may be formed of metal, such as stainless steel. Alternatively, the needle 932 may be inserted into the split introducer 930, and the assembly introduced through the superficial tissue 900, the dura matter 910 and into the CSF 920. A guidewire 656 is then introduced through the needle 932 and the guidewire 656 is then left in place. The needle 932 is then removed, leaving the split introducer 930 and guidewire 656 in place. The catheter 610 (see FIG. 9A) is then introduced over the guidewire 656 as shown in FIG. 17, the guidewire 656 traveling within the guidewire lumen (reference numeral 654 in FIG. 9A). Once the catheter 650 is in place, the split introducer 930 may be peeled off and removed. As shown in FIG. 18, a subcutaneous pocket 934 may then be formed between the superficial tissue 900 and the dura matter 910, and the pump 610 may then be tunneled therein and the pocket 934 sutured close at 935a. Alternatively, the dura matter 910 may sutured close around catheter 650 at 935b before the superficial tissue 900 is sutured. As shown in FIG. 18, the distal end of the catheter 650 is disposed at the desired location within the CSF 920 where the pharmaceutical agent 936 may be released.

Electromechanical implantable pumps are rather large devices and are designed to deliver relatively large volumes of drugs to the patient, whether intravenously, epidurally or intrathecally. The implantable pump system for long-term delivery of a pharmaceutical agent at selectable rates according to the present invention, however, is a smaller device able to deliver a minute, continuous and step-wise selectable flow of a pharmaceutical agent for a long period of time, such as about 6 or 12 months. Consequently, the procedure required to implant the pump system according to the present invention is a less traumatic and simpler procedure than is traditionally required to implant relatively larger electromechanical devices.

For illustrative purposes only and with particular reference to FIGS. 9A and 10, the length of the pump 610, 700 may be about 1.25 inches and the diameter thereof may be about 0.14 inches. The pharmaceutical agent compartment (see reference 202 in FIGS. 2 through 8 and reference 708 in FIG. 10) of such a pump 610, 700 may contain about 0.32 milliliters (ml) of drug or other pharmaceutical agent. Continuing with the same example, the length of the catheter 650 may be about 12 inches with an ID of 0.0025 inches, for a dead space volume (primer volume) therein of about 0.001 ml. A small dead space volume means that the time required for the pharmaceutical agent to reach its destination from the pharmaceutical agent compartment is short. Such an osmotic pump-catheter assembly according to the present invention may infuse about 1.75 microliters (μL) of a drug per day for about 180 days, or about 6 months. For a larger infusion rate of about, for example, 5 μL per day for a period of about 180 days, the length of the pump 610, 700 may be about 1.25 inches and the diameter thereof may be about 0.24 inches. The pharmaceutical agent compartment (see reference 202 in FIGS. 2 through 8 and reference 708 in FIG. 10) of such a pump 610, 700 may contain about 0.9 ml of drug or other pharmaceutical agent. The length of the catheter 650 may be about 12 inches with an ID of 0.005 inches, for a dead space volume therein of about 0.0038 ml. To offer significant pain relief while delivering only about 1 to about 5 μL per day (defined as a 24 hour period), the pharmaceutical agent contained in the compartment 202, 708 must be a potent analgesic agent. The opioids (morphine, for example) conventionally used in implantable pumps would not be therapeutically effective in controlling pain at the above-cited infusion rates. According to the present invention, the pharmaceutical agent compartment 202, 708 may contain sufentanil (such as sufentanil citrate), an opioid that is about 700 to 1,000 times more potent than morphine. This greater potency allows a small volume of drug to alleviate significant pain.

Table 3 is provided to allow a comparison of the dosage needed to achieve a same analgesic effect, across different modes of delivery using the implantable pump system according to the present invention.

TABLE 3

|  | Equianalgesic Conversion factor |
| --- | --- |
| Oral | 300 |
| Intravascular | 100 |
| Subcutaneous | 100 |
| Epidural | 10 |
| Intrathecal | 1 |

As can be seen, delivering an analgesic within the intrathecal space requires a dosage that is 300 hundred times smaller than the dosage needed to achieve the same analgesic effect when the drug is given orally. There is, however, not a direct correlation in the equianalgesic conversion chart for the intravascular and subcutaneous routes. Indeed, as the patient's need for more medication increases, they will be converted to other modes of delivery.

Table 4 illustrates the starting and expected maximum dosage range of sufentanil using the implantable pump system of the present invention, as the system is implanted intravascularly, subcutaneously, epidurally, intrathecally and intraventricularly, according to further embodiments of the present invention.

TABLE 4

|  | Starting Dosage Range (μg/day) | Expected Maximum Dosage (μg/day) |
| --- | --- | --- |
| Intravascular | 10–100 | 300 |
| Subcutaneous | 10–100 | 300 |
| Epidural | 5.0–50 | 300 |

TABLE 4-continued

|  | Starting Dosage Range (μg/day) | Expected Maximum Dosage (μg/day) |
|---|---|---|
| Intrathecal | 0.5–5.0 | 50 |
| Intraventricular | 0.5–2.5 | 25 |

While the foregoing detailed description has described preferred embodiments of the present invention, it is to be understood that the above description is illustrative only and not limiting of the disclosed invention. Moreover, Those of skill in this art will recognize other alternative embodiments and all such embodiments are deemed to fall within the scope of the present invention. Thus, the present invention should be limited only by the claims as set forth below.

What is claimed is:

1. An implantable osmotic pump system for delivering a pharmaceutical agent to a patient, comprising:
   an implantable pump, including:
      a pump housing;
      a moveable partition disposed within the housing, the partition dividing the housing into an osmotic driving compartment having an open end and a pharmaceutical agent compartment having a delivery orifice;
      a first semi permeable membrane disposed in the open end of the osmotic driving compartment, the first semi permeable membrane being exposed to the patient;
      a second semi permeable membrane disposed in the open end of the osmotic driving compartment, and
      a first impermeable barrier disposed over the second semi permeable membrane, the second semi permeable membrane being sealed from the patient until the first barrier is breached, wherein breaching the first barrier increases the surface area of semi permeable membrane exposed to the patient and increases a delivery rate of a pharmaceutical agent through the delivery orifice.

2. The pump system of claim 1, wherein the first impermeable barrier includes at least one of titanium and stainless steel.

3. The pump system of claim 1, further comprising a saturated solution including NaCl between the first impermeable barrier and the second semi permeable membrane.

4. The pump system of claim 1, wherein the first and second semi permeable membranes have a same composition.

5. The pump system of claim 1, wherein the first and second semi permeable membranes have a same thickness.

6. The pump system of claim 1, wherein the first and second semi permeable membranes have mutually different compositions.

7. The pump system of claim 1, wherein the first and second semi permeable membranes have mutually different thickness.

8. The pump system of claim 1, further including:
   a third semi permeable member, and
   a second impermeable barrier, the second impermeable barrier being disposed over the third semi permeable membrane, the third semi permeable membrane being sealed from the patient until the second impermeable barrier is breached, wherein breaching the second barrier increases the surface area of semi permeable membrane exposed to the patient and increases a delivery rate of the pharmaceutical agent through the delivery orifice.

9. The pump system of claim 8, further comprising a saturated solution including NaCl between the second barrier and the third semi permeable membrane.

10. The pump system of claim 1, wherein the pharmaceutical agent compartment contains sufentanil.

11. The pump system of claim 10, wherein the sufentanil is at a concentration selected between about 200 μg/mL and about 15,000 μg/mL.

12. The pump system of claim 1, wherein the delivery rate of the pharmaceutical agent through the delivery orifice is selected from about:
   0.5 micrograms per day to about 25 micrograms per day when the pump is configured to deliver the pharmaceutical agent intraventricularly;
   0.5 micrograms per day to about 50 micrograms per day when the pump is configured to deliver the pharmaceutical agent intrathecally;
   5 micrograms per day to about 300 micrograms per day when the pump is configured to deliver the pharmaceutical agent epidurally, and
   10 micrograms per day to about 300 micrograms per day when the pump is configured to deliver the pharmaceutical agent subcutaneously.

13. The pump system of claim 1, wherein the first and second semi permeable membranes include cellulose acetate.

14. The pump system of claim 1, wherein the first semi permeable membrane is shaped as a torus and is disposed adjacent an outer periphery of the first impermeable barrier and wherein the second semi permeable membrane is disposed in a center opening of the torus.

15. The pump system of claim 1, further comprising a catheter coupled to the delivery orifice.

16. The pump system of claim 15, wherein the catheter has an inner diameter of between about 0.001 inches and about 0.010 inches.

17. The pump system of claim 15, wherein the catheter includes a guidewire lumen and a pharmaceutical agent infusion lumen.

18. The pump system of claim 17, wherein the pharmaceutical agent infusion lumen has an inner diameter selected between about 0.001 inches to about 0.010 inches.

19. The pump system of claim 17, wherein the guidewire lumen includes a valve to prevent back flow of fluid into the guidewire lumen.

20. The pump system of claim 15, wherein the catheter and the pump are dimensioned to infuse a volume of pharmaceutical agent of between about 1 μL/day and about 10 μL/day over a treatment period.

21. The pump system of claim 15, wherein the catheter and the pump are dimensioned to infuse a dose of pharmaceutical agent of between about 0.5 μg/day and about 300 μg/day over a treatment period.

22. The pump system of claim 15, wherein at least a portion of the catheter is radiopaque.

23. An integrated implantable pump and catheter system for delivering a dose of pharmaceutical agent to a patient over a treatment period, comprising:
   a pump housing;
   a moveable partition disposed within the housing, the partition dividing the housing into an driving engine compartment and a pharmaceutical having an open end agent compartment having a delivery orifice;

a catheter coupled to the delivery orifice;

a preloaded amount of pharmaceutical agent in the pharmaceutical agent compartment, and a mechanical an infusion rate selection structure disposed within the open end configured to allow the infusion rate of the pump to be increased while the system is implanted in the patient, the infusion rate selection structure including a plurality of semi permeable membranes, wherein selectively exposing a surface area of the plurality of semipermeable membranes to the patient increases the infusion rate of the pharmaceutical agent.

24. The system of claim 23, wherein the pump and catheter are dimensioned to deliver sufentanil at an infusion rate of about 0.5 µg/day to about 300 µg/day over a treatment period.

25. The system of claim 23, wherein each of the plurality of semi permeable membranes has a selected thickness, composition and surface area, the selected thickness, composition and surface area contributing to a rate at which the pharmaceutical agent is infused into the patient.

26. A method of delivering a pharmaceutical agent to a patient, comprising the steps of:

implanting an osmotic pump within the patient, the osmotic pump including a pump housing, a moveable partition disposed within the housing, the partition dividing the housing into a driving engine compartment having an open end and a pharmaceutical agent compartment, a preloaded amount of the pharmaceutical agent in the pharmaceutical agent compartment, and a mechanical infusion rate selection structure disposed within the open end configured to allow an infusion rate of the pump to be increased while the pump is implanted in the patient, the infusion rate selection structure including a plurality of semi-permeable membranes, and controlling a surface area of the plurality of the semi permeable membranes exposed to the patient to control and infusion rate of the pharmaceutical agent to the patient.

27. The method of claim 26, further comprising the step of controlling at least one of a thickness and a composition of each of the plurality of semi permeable membranes.

28. The system of claim 23, wherein the pharmaceutical agent includes Sufentanil.

29. The pump of claim 28, wherein each of the plurality of semi permeable membranes has a selected thickness, composition and surface area, the selected thickness, composition and surface area contributing to a rate at which the pharmaceutical agent is infused into the patient.

30. An implantable pump for delivering a dose of pharmaceutical agent to a patient over a treatment period, comprising:

a pump housing;

a moveable partition disposed within the housing, the partition dividing the housing into an driving engine compartment and a pharmaceutical agent compartment having a delivery orifice;

a preloaded amount of pharmaceutical agent in the pharmaceutical agent compartment, and a mechanical infusion rate selection structure configured to allow the infusion rate of the pump to be increased while the system is implanted in the patient, the infusion rate selection structure including a plurality of semi permeable membranes, wherein selectively exposing a surface area of the plurality of semipermeable membranes to the patient increases the infusion rate of the pharmaceutical agent.

31. The pump of claim 30, wherein the pump is dimensioned to deliver the pharmaceutical agent at an infusion rate of about 0.5 µg/day to about 300 µg/day over the treatment period.

32. The pump of claim 30, wherein the pharmaceutical agent includes Sufentanil.

* * * * *

UNITED STATES PATENT AND TRADEMARK OFFICE
CERTIFICATE OF CORRECTION

PATENT NO. : 6,436,091 B1  Page 1 of 1
DATED : August 20, 2002
INVENTOR(S) : Harper et al.

It is certified that error appears in the above-identified patent and that said Letters Patent is hereby corrected as shown below:

Column 20,
Lines 6-8, should read as follows:
-- partition dividing the housing into a driving engine compartment having an open end and a pharmaceutical agent compartment having a delivery orifice; --

Column 21,
Line 18, please insert -- an -- and delete "and".

Column 22,
Line 13, please insert -- pump -- and delete "system".

Signed and Sealed this

Twenty-fourth Day of December, 2002

JAMES E. ROGAN
*Director of the United States Patent and Trademark Office*